United States Patent [19]

Heidt et al.

[11] Patent Number: 5,412,151
[45] Date of Patent: May 2, 1995

[54] THERMOSETTING COATING COMPOSITIONS

[75] Inventors: Philip C. Heidt; Charles H. Foster, both of Kingsport, Tenn.; J. Stewart Witzeman, Den Haag, Netherlands; Allen L. Crain, Church Hill, Tenn.

[73] Assignee: Eastman Chemical Company, Kingsport, Tenn.

[21] Appl. No.: 139,661

[22] Filed: Oct. 22, 1993

[51] Int. Cl.$^6$ .............................................. C07C 59/305
[52] U.S. Cl. .................................. 560/145; 560/146; 560/176
[58] Field of Search ..................... 560/145, 146, 176; 554/227

[56] References Cited

U.S. PATENT DOCUMENTS

| | | | |
|---|---|---|---|
| 4,795,787 | 1/1989 | Walz | 525/328.2 |
| 5,247,122 | 9/1993 | Witzeman et al. | 560/51 |

OTHER PUBLICATIONS

Witzeman et al., "Transacetoacetylation w/t-butyl Acetoacetate": Synthetic Applications, (1990) J. Org. Chemistry v. 56, 1713–1718.

W. Murray, M. Wachter, D. Barton and Y. Forero–Kelly, Synthesis, 18, (1991).
W. Murray, M. Wachter, J. Org. Chem., 55, 3424, (1990).
J. S. Witzeman, Tetrahedron Letters, 31, 1401, (1990).
S. S. Labana, Encyclopedia of Polymer Science and Engineering, vol. 4, pp. 350–395.
F. P. Montforts and S. Ofner, Angew: Chem. Int. Ed. Engl. 18 (1979), No. 8, 632.
J. Chem. Soc., 2821, (1971).
S. Ohta, A. Tsujimura and M. Okamoto, Chem. Pharm. Bull., 29, 2762, (1981).

*Primary Examiner*—James J. Seidleck
*Assistant Examiner*—Patrick R. Delaney
*Attorney, Agent, or Firm*—Bernard J. Graves, Jr.; Harry J. Gwinnell

[57] ABSTRACT

Provided are 3-oxoadipate esters of certain polyols which are useful as crosslinkers in thermosetting coating compositions. Also provided are such thermosetting compositions comprised of a curable hydroxyl-functional polymer such as a polyester or acrylic and the crosslinkers of the present invention. Such compositions offer a significant improvement in curing temperature.

5 Claims, No Drawings

THERMOSETTING COATING COMPOSITIONS

FIELD OF THE INVENTION

The invention relates to 3-oxoadipate esters of certain polyols which are useful as crosslinkers in thermosetting coating compositions.

BACKGROUND OF THE INVENTION

Crosslinkers are multi-functional molecules capable of reacting with pendant functional groups on polymers. The use of crosslinkers enables one to increase the molecular weight of the resin or polymer and thus improve the properties of the resulting polymer or polymeric film. Most crosslinking reactions are initiated by heating a mixture of the polymer and the crosslinker either neat or in a solvent. Such systems are often referred to as "thermosetting" systems.

Crosslinkers are particularly useful in coating applications due to the fact that the crosslinker enables the use of relatively low molecular weight polymers and resins which are easily handled and applied in solvents. The formulation can subsequently be applied to the substrate and heated, or cured, to give the finished (thermoset) coating. This makes it possible to take advantage of the ease of handling and solubility characteristics of the lower molecular weight resins used in the formulation and subsequently develop the hardness, chemical and solvent resistance, as well as strength properties desired in the ultimate coating by the reaction of the crosslinker with the resin during the curing process.

Crosslinkers are becoming increasingly important due to the emphasis on more environmentally acceptable coatings. One major environmental concern in the coatings industry is the amount of organic solvent released during the curing process. This solvent level or Volatile Organic Content (VOC) is of concern due to the role of organic solvents in the development of photochemical smog. For these reasons various governments, including the U.S., are regulating the VOC levels of coating formulations. One way to reduce the amount of solvent necessary in a coating formulation is to reduce the molecular weight of the resin backbone used in the formulation. When this approach is used, however, crosslinking becomes even more critical to the development of the ultimate properties in the cured film. Thus, in these applications the crosslinker enables a more environmentally sound coating formulation.

Properties of Crosslinked Films and Coatings

A number of properties are desired in a coating in order to impart the desired protection of the object from corrosion and other environmental factors. Some of the protective characteristics that are ultimately desired include the resistance of the coating to various chemicals and solvents, the impact strength of the system, the hardness of the coating and the weatherability, or resistance, of the system to various factors related to environmental exposure.

I) Chemical and Solvent Resistance

In order for a coating to impart adequate protection to the object coated it must be resistant to various chemicals and solvents. If a coating is not resistant to solvents and chemicals the coating could be removed or the protective integrity compromised by exposure to commonly used materials such as cleaners or gasoline. A commonly used test to assay this property is the methyl ethyl ketone (MEK) rub resistance of the coating. The MEK rub resistance of a coating is one of the most widely used diagnostic tests for crosslinking in coatings. For most applications, an MEK rub resistance of greater than 175–200 is desired.

II) Impact Strength

In order for a coating to be resistant to collisions and other sudden impacts the material must have certain strength characteristics. If a coating does not possess enough strength, impacts and/or collisions will lead to chipping and breaking of the coating which, in turn, compromise the protective integrity of the film. A commonly used test for the impact strength of a coating (ASTM D2794-84) is performed by dropping a weight from various heights on a coated panel and determining the foot-lbs of force required to break the coating. Proper crosslinking contributes to the impact strength of a coating.

III) Hardness

In order for a coating to be resistant to scratching and other such abrasions the coating must possess a certain degree of hardness. This resistance to scratching is often determined by marring the coating with pencils of various hardness and noting which hardness of pencil actually scratches the coating.

Hardness and impact strength often work in opposite directions. This is due to the fact that impact strength reflects both the strength and the flexibility of the polymeric film, while hardness reflects primarily just the strength, or rigidity of the film. Thus, one often seeks a combination of hardness and flexibility by compensating one of the above characteristics for the other.

The compensation of these two factors is best understood by invoking the theory of crosslink density. If the coating formulation consists of a group of polyfunctional (n>2) polymer molecules and crosslinker then the crosslinking process can be thought of as consisting of a series of steps. Initially, the crosslinking reaction consists of intermolecular reactions of various polymer chains. During this initial phase the chains are combining and thus building in molecular weight, but, the mobility of the polymer chains is not greatly restricted. This stage would be characterized by improvement in the chemical resistance, hardness and impact strength of the film. At some point, however, intermolecular reaction is essentially complete and intramolecular reaction becomes significant. At this point, the polymer becomes more rigid due to restriction of the polymer chain mobility by these intramolecular reactions and the resulting coating becomes more brittle. At this stage, hardness will improve but the impact strength will decrease due to the increased rigidity of the polymer network. The balance between flexibility and hardness can be controlled by the amount of crosslinker used, the average functionality of the polymer and crosslinker as well as the chemical structure of the polymer or crosslinker.

IV) Resistance to Atmospheric Exposure (Weathering)

Since many coated objects are exposed to severe weather conditions, the performance of the coating under various exposure conditions is very important. Factors which affect the weatherability of the coating include the composition of the polymer and the crosslinker, as well as the degree of crosslinking. A variety of exposure tests are available which enable one to determine the performance of the system to severe conditions.

Crosslinkers Currently Used in the Field

A large number of crosslinkers are used in various applications. A partial list of the more common types of compounds used as crosslinkers include:
Polyepoxides
Polyisocyanates
Amino resins (e.g. melamines)
Polyunsaturated compounds These materials take advantage of the reaction of the aforementioned functional groups with various pendant groups on the polymeric backbone. These crosslinkers can be used in combination with other crosslinkers to impart a variety of desired characteristics to the coatings. The use and reactions of these crosslinkers have been reviewed elsewhere. Bisacetoacetates of general formula 1 have been shown to act as a crosslinker and is the subject of U.S. Pat. No. 5,247,122.

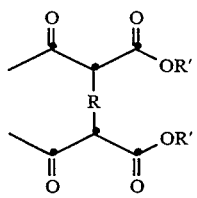

Very few examples of compounds which contain both beta-ketoester and carboxylic acid functionalities are known. The preparation of beta-ketoadipic acid esters has been described (Montforts, F. P., Silvio, S., *Angew Chem. Int. Ed.*, 632 (1979). German Patent DE 2,222,926 (Nov. 23, 1972) describes the preparation of ethyl 4-carboxybenzoylacetates. The ortho and meta analogues of this compound have also been described (Buckle, D. and Smith, H., *J. Chem. Soc. C*, 2821 (1971). The preparation and use of t-butyl and methyl beta-ketoglutarate in the preparation of 4-hydroxy-2-pyrones has also been discussed. (Ohta, S. Tsujimara, A., and Okamoto, M., *Chem. Pharm. Bull.*, 29, 2762, (1981).)

Compounds which possess a 1,3-diketone moiety and carboxylic acid groups are also known, Murray, W., Wachter, M., Barton, D., and Forrero-Kelley, Y., Synthesis, 18, (1991), Murray, W. and Wachter, M., J. Org. Chem., 55, 3424, (1990). These systems do not possess the essential ester group necessary to be of use in coatings and polymer chemistry.

U.S. Pat. No. 4,795,787 describes the Michael addition products of monocarboxylic or dicarboxylic acid esters capable of undergoing Michael addition with compounds containing at least two double bonds are taught to be useful as crosslinkers in coating systems utilizing amine-containing or hydroxyl-containing resins.

SUMMARY OF THE INVENTION

This invention provides 3-oxoadipate esters of polyols which are useful as crosslinkers in thermosetting coating compositions. The crosslinkers of the present invention can be blended with a curable hydroxyl-functional polymer and a suitable solvent to form such compositions. Surprisingly, the compositions of the present invention cure at a significantly lower temperature than do conventional hydroxyl polymer/crosslinker systems.

DETAILED DESCRIPTION OF THE INVENTION

The present invention provides a compound of formula (2)

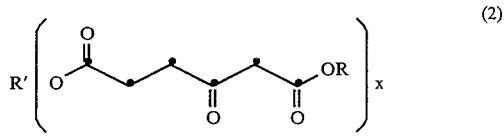

wherein
R is $C_1$-$C_6$ alkyl or phenyl;
R' is the residue of a polyol selected from the group consisting of trimethylolpropane, trimethylolethane, pentaerythritol, glycerine, glucose, sucrose, and a low molecular weight polyol having a Mn of about 250 to 1000; and
x is an integer from 2 to 12.

Compounds of formula (2) can be prepared by reacting an acetoacetate of the formula

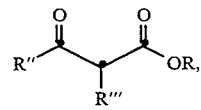

wherein
R is $C_1$-$C_6$ alkyl or phenyl;
R'' is $C_1$-$C_{30}$ alkyl; and
R''' is $C_1$-$C_{30}$ alkyl
with succinic anhydride or a succinyl halide in the presence of base, followed by reaction with a polyhydroxyl compound of the formula R'(OH)$_x$, wherein R' and x are as described above. A preferred polyhydroxyl compound is low molecular weight polyol having a Mn of about 250 to 1000 such as a polyester polyol, a polyether polyol, a polyamide polyol, a polyester ether polyol, a polyamide ester polyol, a polyether amide polyol, a polyether ester amide polyol, or a polyurethane polyol. As a further aspect of the present invention there is provided this process.

In this process, examples of preferred bases include sodium hydride, potassium hydride, sodium hydroxide, potassium hydroxide, potassium t-butoxide, 1,5-diazabicyclo [4.3.0]non-5-ene, 1,8-diazabicyclo [5.4.0]undec-7-ene and the like.

The compounds of formula (2) above are useful as crosslinking agents in thermosetting coating compositions which utilize hydroxyl-functional resins as binders. Thus, in a further embodiment of the present invention, there is provided a thermosetting coating composition comprising
(a) a hydroxyl-functional polymer; and
(b) a compound of formula (2).

The polymer or resin can be any hydroxylated polymer or resin such as an acrylic or a polyester. The acrylic component is a polymer or resin prepared by polymerization of a hydroxyl-bearing monomer such as hydroxyethyl methacrylate, hydroxyethyl acrylate, hydroxyhexyl acrylate, hydroxyhexyl methacrylate, hydroxypropyl acrylate, hydroxypropyl methacrylate, hydroxybutyl acrylate, hydroxybutyl methacrylate and the like optionally polymerized with other monomers such as methyl acrylate, methyl methacrylate, ethyl acrylate, ethyl methacrylate, butyl acrylate, butyl methacrylate, isobutyl acrylate, isobutyl methacrylate, ethylhexyl acrylate, ethylhexyl methacrylate, styrene, vinyl acetate, and the like. The polyester consists of a resin or polymer prepared by condensation of a slight excess of polyol with a polycarboxylic acid. Examples of polyols that can be used are ethylene glycol, propylene glycol, butanediol, pentanediol, hexanediol, 2-methylpropanediol, 1,3-propanediol, neopentylglycol, 2,2,4-trimethyl-1,3-propanediol, 3-methylpentanediol, trimethylolpropane, trimethylolethane, 1,4-cyclohexanedimethanol, 1,3-cyclohexanedimethanol, and the like. Examples of polycarboxylic acids include aromatic diacids such as terephthalic acid, isophthalic acid, and phthalic acid; aliphatic diacids such as malonic acid, succinic acid, glutaric acid, adipic acid, 1,4-cyclohexanedicarboxylic acid, 1,3-cyclohexanedicarboxylic acid, and the like. The ratio of reagents and molecular weights of the resulting acrylic or polyester are chosen so as to give polymers with an average functionality (the number of OH groups per molecule) greater than or equal to 2, preferably greater than or equal to 4.

The exact ratio of crosslinker to polymer or resin will depend on the molecular weight and functionality of each species. Preferably, however, the following proportions of material will be used:

(a) about 15 to 80 percent, based on the weight of the total composition of polyester or acrylic.
(b) about 0 to 50 percent, based on the weight of the total composition of solvent.
(c) about 10 to 40 percent, based on the weight of the crosslinker described above.

Preferred amounts of (a) are about 30 to 70 percent; more preferred are about 45 to 55 percent.

Preferred amounts of (b) are about 0 to 40 percent; more preferred are about 0 to 35 percent.

Preferred amounts of (c) are about 10 to 38 percent; more preferred are about 10 to 35 percent.

The crosslinker system can include the 3-oxoadipate esters of polyols described above by themselves or used in conjunction with other crosslinkers such as melamines, isocyanates, and epoxys.

The formulation can be applied to any object such as metal, glass, plastic and the like. The formulation is crosslinked, or cured, by heating the material at 100°–250° C. for 1 min to 2 hours with 150°–230° C. for 5–45 min being preferred.

Compounds of formula (2) above, wherein R' is hydrogen, i.e.,

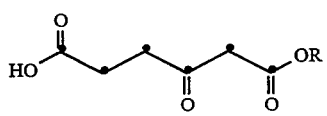

can be reacted with a compound of the formula

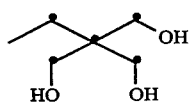

in the presence of a condensing agent, to provide a compound of formula (3)

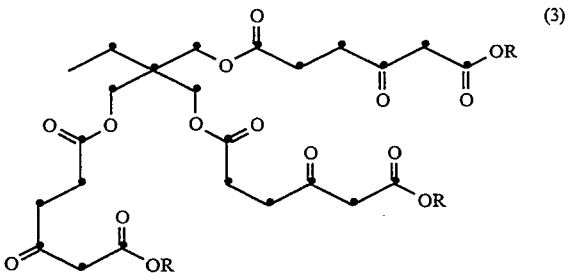

wherein R is as described above. Compounds of formula (3) are useful as crosslinkers in thermosetting coating compositions which utilize a hydroxyl-functional polymer as binder.

In the above reaction, suitable reaction conditions and condensing agents are well-known and can be chosen, for example, from the following:

a) Dicyclohexylcarbodiimide/N,N-dimethylaminopyridine;
b) p-Toluenesulfonic acid/benzene/heat;
c) carbonyldiimidazole, sodium methoxide, heat;
d) methanesulfonyl chloride/triethylamine, N,N-dimethylaminopyridine;
e) cyanuric chloride/triethylamine; or
f) triphenylphosphine/carbon tetrachloride/triethylamine.

Dicyclohexylcarbodiimide/N,N-dimethylaminopyridine is preferred.

Thus, as a further aspect of the present invention, there is provided a thermosetting coating composition which comprises (a) a hydroxyl-functional polymer; and
(b) a compound of formula (3).

The exchange reaction of acetoacetates has been shown to proceed via the intermediacy of acetylketene (4).

The crosslinking process is believed to involve a similar tris(acetylketene), (5).

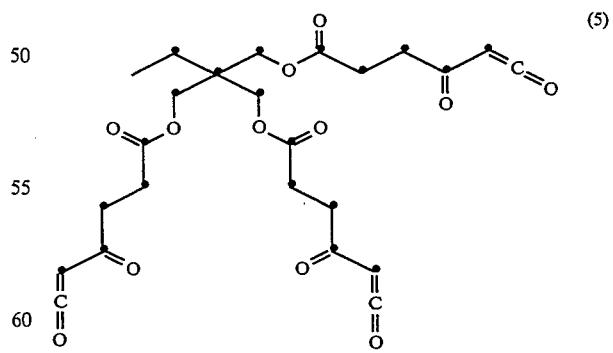

Suitable solvents for the curable enamel composition include xylenes, toluene, ketones, (for example, cyclohexanone, methyl amyl ketone, methyl ethyl ketone, methyl isobutyl ketone, diisobutyl ketone, and the like), 2-butoxyethanol, ethyl 3-ethoxypropionate, n-butanol, ester solvents such as ethyl acetate, butyl acetate, propyl acetate, and the like; alcohols such as butanol, other solvents such as ethoxyethyl propionate (EEP), and other volatile inert solvents typically used in industrial baking (i.e., thermosetting) enamels.

In a further aspect of the present invention, the compositions may also contain an amino cross-linking agent.

The "amino cross-linking agent" is preferably a melamine-type cross-linking agent, i.e., a cross-linking agent having a plurality of —N(CH$_2$OR$^3$)$_2$ functional groups, wherein R$^3$ is C$_1$–C$_4$ alkyl, preferably methyl.

In general, the amino cross-linking agent may be selected from compounds of the following formulae, wherein R$^3$ is independently C$_1$–C$_4$ alkyl:

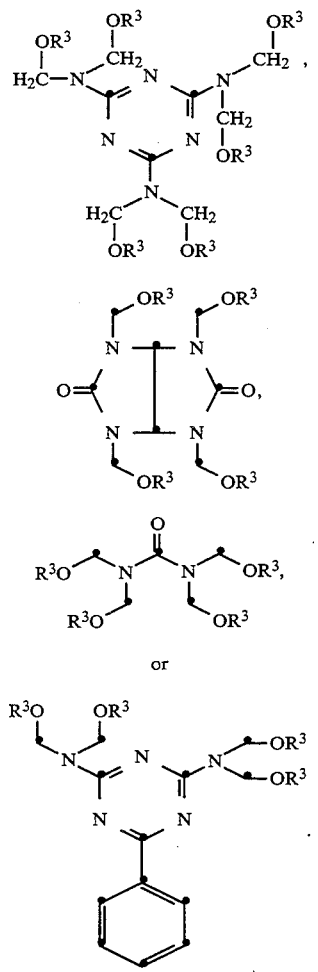

In this regard, preferred amino cross-linking agents include hexamethoxymethylmelamine, tetramethoxymethylbenzoguanamine, tetramethoxymethylurea, mixed butoxy/methoxy substituted melamines, and the like. The most preferred amino cross-linking agent is hexamethoxymethylmelamine.

As a further aspect of the present invention, there is provided a curable enamel composition further comprising one or more cross-linking catalysts. Examples of cross-linking catalysts for melamine type cross-linking agents include p-toluenesulfonic acid and NACURE ™ 155, 5076, 1051, catalysts sold by King Industries.

As a further aspect of the present invention there is provided a cross-linkable enamel composition as described above, further comprising one or more leveling, rheology, and flow control agents such as silicones, fluorocarbons or cellulosics; flatting agents; pigment wetting and dispersing agents; surfactants; ultraviolet (UV) absorbers; UV light stabilizers; tinting pigments; defoaming and antifoaming agents; anti-settlings anti-sag and bodying agents; anti-skinning agents; anti-flooding and anti-floating agents; fungicides and mildewcides; corrosion inhibitors; thickening agents; or coalescing agents.

Specific examples of such additives can be found in Raw Materials Index, published by the National Paint & Coatings Association, 1500 Rhode Island Avenue, N.W., Washington, D.C. 20005.

Examples of flatting agents include synthetic silica, available from the Davison Chemical Division of W. R. Grace & Company under the trademark SYLOID ®; polypropylene, available from Hercules Inc., under the trademark HERCOFLAT ®; synthetic silicate, available from J. M. Huber Corporation under the trademark ZEOLEX ®.

Examples of dispersing agents and surfactants include sodium bis(tridecyl) sulfosuccinnate, di(2-ethyl hexyl) sodium sulfosuccinnate, sodium dihexylsulfosuccinnate, sodium dicyclohexyl sulfosuccinnate, diamyl sodium sulfosuccinnate, sodium diisobutyl sulfosuccinnate, disodium iso-decyl sulfosuccinnate, disodium ethoxylated alcohol half ester of sulfosuccinnic acid, disodium alkyl amido polyethoxy sulfosuccinnate, tetrasodium N-(1,2-dicarboxy-ethyl)-N-oxtadecyl sulfosuccinnamate, disodium N-octasulfosuccinnamate, sulfated ethoxylated nonylphenol, 2-amino-2-methyl-1-propanol, and the like.

Examples of viscosity, suspension, and flow control agents include polyaminoamide phosphate, high molecular weight carboxylic acid salts of polyamine amides, and alkyl amine salt of an unsaturated fatty acid, all available from BYK Chemie U.S.A. under the trademark ANTI TERRA ®. Further examples include polysiloxane copolymers, polyacrylate solution, cellulose esters, hydroxyethyl cellulose, hydrophobically-modified hydroxyethyl cellulose, hydroxypropyl cellulose, polyamide wax, polyolefin wax, carboxymethyl cellulose, ammonium polyacrylate, sodium polyacrylate, and polyethylene oxide.

Several proprietary antifoaming agents are commercially available, for example, under the tradename Brubreak of Buckman Laboratories Inc., under the BYK ® trademark of BYK Chemie, U.S.A., under the FOAMASTER ® and NOPCO ® trademarks of Henkel Corp./Coating Chemicals, under the DREWPLUS ® trademark of the Drew Industrial Division of Ashland Chemical Company, under the TROYSOL ® and TROYKYD ® trademarks of Troy Chemical Corporation, and under the SAG ® trademark of Union Carbide Corporation.

Examples of fungicides, mildewcides, and biocides include 4,4-dimethyloxazolidine, 3,4,4-trimethyloxazolidine, modified barium metaborate, potassium N-hydroxy-methyl-N-methyldithiocarbamate, 2-(thiocyanomethylthio) benzothiazole, potassium dimethyl dithiocarbamate, adamantane, N-(trichloromethylthio) phthalimide, 2,4,5,6-tetrachloroisophthalonitrile, orthophenyl phenol, 2,4,5-trichlorophenol, dehydroacetic acid, copper naphthenate, copper octoate, organic arsenic, tributyl tin oxide, zinc naphthenate, and copper 8-quinolinate.

Examples of U.V. absorbers and U.V. light stabilizers include substituted benzophenone, substituted benzotriazole, hindered amine, and hindered benzoate, available from American Cyanamide Company under the trademark CYASORB UV, and available from Ciba Geigy under the trademark TINUVIN, and diethyl-3-acetyl-4-hydroxy-benzyl-phosphonate, 4-dodecyloxy-2-hydroxy benzophenone, and resorcinol monobenzoate.

Such paint or coating additives as described above form a relatively minor proportion of the enamel composition, preferably about 0.05 weight percent to about 5.00 weight percent.

As a further aspect of the present invention, there is provided a curable enamel composition optionally containing one or more of the above-described additives, further comprising one or more pigments.

Pigments suitable for use in the enamel compositions envisioned by the present invention are the typical organic and inorganic pigments, well-known to one of ordinary skill in the art of surface coatings, especially those set forth by the *Colour Index*, 3d Ed., 2d Rev., 1982, published by the Society of Dyers and Colourists in association with the American Association of Textile Chemists and Colorists. Examples include but are not limited to the following: CI Pigment White 6 (titanium dioxide); CI Pigment Red 101 (red iron oxide); CI Pigment Yellow 42, CI Pigment Blue 15, 15:1, 15:2, 15:3, 15:4 (copper phthalocyanines); CI Pigment Red 49:1, and CI Pigment Red 57:1.

Upon formulation above, the curable enamel composition is then applied to the desired substrate or article, e.g., steel, aluminum, or galvanized sheeting (either primed or unprimed), heated (i.e., cured) to a temperature of about 140° C. to about 175° C., for a time period of 5–60 minutes and subsequently allowed to cool. Thus, as a further aspect of the present invention, there is provided a shaped or formed article which has been coated with the thermosetting coating compositions of the present invention and cured.

Further examples of typical application and curing methods can be found in U.S. Pat. Nos. 4,737,551 and 4,698,391, incorporated herein by reference.

As a further aspect of the present invention, there is provided a coating which results from the application and curing of the curable enamel composition as set forth above.

Experimental Section

General $^1$H and $^{13}$C NMR spectra were obtained on a Varian Model Gemini 300 in $CDCl_3$ at frequencies of 300 and 75 MHz respectively.

The applicable test procedures are as follows:
1. Testing Coated Metal Specimens at 100 Percent Relative Humidity—Cleveland Humidity Test (ASTM Method D 2247)
2. Film Thickness (General Electric Gage, Type B)
3. Film Hardness (Pencil Method, ASTM 3363-74, Reapproved 1980)
4. Solvent Resistance (methyl ethyl ketone (MEK) dynamic rub test, ASTM Method D 1308)
5. Impact Resistance (ASTM Method D 2794-84)
6. Resin molecular weight-GPC
7. OH Value determined by titration and are in units of mg KOH consumed per gram of polymer.
8. Acid Number (ASTM Method D 465). The units of this value are the same as the OH value.

The following resins were used in the evaluations:

RESIN A: This material was a polyester prepared using a two-stage addition procedure from 2.47 moles neopentyl glycol, 0.78 moles trimethylolpropane, 1.73 moles 1,4-cyclohexane dicarboxylic acid, and 1.17 moles phthalic anhydride. The material had a Mw=23082, a Mn=2692, a hydroxyl value of 103, and an acid value of 4.5. This material was thinned with xylene and used as a 75% solids solution.

RESIN B: Same as Resin A except a hydroxyl value of 104, an acid value of 9, a Mw=12160, and a Mn=4300. This material was thinned with xylene and used as a 75% solids solution.

EXAMPLE 1

Preparation of the Mono t-Butyl Ester of 3-Oxoadipic Acid

To a well-stirred suspension of sodium hydride (21.3 g of a 60% dispersion in oil, 0.53 mol) in tetrahydrofuran (500 mL) under nitrogen at 0° C. was added t-butyl acetoacetate (79.1 g, 0.50 mol) dropwise over 30 minutes. A clear solution resulted which was stirred an additional one hour before succinic anhydride (50.0 g, 0.50 mol) was added in portions over 10 minutes. Within 10 minutes, the solution gelled and after 45 minutes, stirring was achieved again. The mixture was then refluxed one hour, cooled to 23° C., then filtered. The moist solid was dissolved in water, acidified with 5M aqueous HCl, then extracted three times with ethyl acetate. The combined extracts were concentrated in vacuo to provide an oily solid which was washed with heptane and suction filtered to provide 38.3 g (30%) of the mono t-butyl ester of 2-acetyl-3-oxoadipic acid. $^1$H NMR (300 MHz, Gemini 300, $CDCl_3$)δ 17.38 (s, 1H), 3.06 (t, J=6.7 Hz, 2H), 2.68 (t, J=6.7 Hz, 2H), 2.32 (s, 3H), 1.54 (s, 9H).

To a well-stirred suspension of the mono t-butyl ester of 2-acetyl-3-oxoadipic acid (5.17 g, 20.0 mmol) in xylene (25 mL) at 23° C. was added dropwise over three minutes, a solution of sodium hydroxide (2.0 g, 50.0 mmol) in water (15 mL). After 16 hours, stirring was stopped and the phases separated. The aqueous phase was acidified to a pH of 2 to 3 with 4M aqueous HCl then extracted with ethyl acetate. The organic phase was concentrated in vacuo, the residue washed with heptane, then filtered to provide 3.85 g (89%) of product as an off-white solid. $^1$H NMR (300 MHz, Gemini 300, $CDCl_3$)δ 3.39 (s, 2H), 2.85 (t, J=6 Hz, 2H), 2.65 (t, J=6 Hz, 2H), 1.46 (s, 9H); $^{13}$C NMR (75 MHZ, Gemini 300, $CDCl_3$, ref. 77.0 ppm)δ 201.2, 177.9, 177.0, 82.2, 50.5, 37.0, 27.9, 27.6.

EXAMPLE 2

Preparation of the Mono t-Butyl Ester of 3-Oxoadipic Acid

A solution of t-butyl acetoacetate (94.92 g, 0.60 mol) in p-xylene (150 mL) was added dropwise to a mechanically-stirred solution of sodium hydroxide (28 g, 0.70 mol) in water (65 mL) at 0° C. After addition, stirring became difficult so an additional amount of p-xylene (50 mL) and water (65 mL) were added. After stirring 10 minutes, half of the succinyl chloride (35.5 mL, 0.32 mol) in p-xylene (125 mL) was added dropwise. Upon addition, the remaining succinyl chloride solution was added dropwise simultaneously with a solution of sodium hydroxide (25 g, 0.63 mol) in water (75 mL). The two-phase mixture was stirred five days at room temperature before the stirring was stopped and the phases separated. The aqueous phase was acidified to a ca. pH of 1-2 with 5M aqueous HCl then extracted with ethyl acetate. The ethyl acetate phase was washed with water then concentrated in vacuo to produce an oily residue which slowly crystallized. The solids were suction filtered and washed twice with petroleum ether to provide 11.28 g (16.3%) of product. $^1$H NMR (300 MHz, Gemini 300, CDCl$_3$)δ 3.39 (s, 2H), 2.85 (t, 2H), 2.64 (t, 2H), 1.45 (s, 9H).

EXAMPLE 3

Preparation of Hexanedioic acid, 3-oxo-, 6,6'-[2-[[[6-(1,1-dimethylethoxy)-1,4,6-trioxohexyl]oxy]methyl]-2-ethyl-1,3-propanediyl]1,1'-bis (1,1-dimethylethyl) ester, 3

To a well-stirred solution of the mono t-butyl ester of 3-oxoadipic acid (10.84 g, 50.0 mmol) in methylene chloride (60 mL) at 0° C. was added trimethylolpropane (1.88 g, 14.0 mmol) followed by dimethylaminopyridine (0.50 g). After stirring 30 minutes, a solution of dicyclohexylcarbodiimide (11.35 g, 55.0 mmol) in methylene chloride (40 mL) was added dropwise over 20 minutes. The mixture was stirred overnight at room temperature and the solids which formed were removed by filtration. The filtrate was washed twice with 1M aqueous HCl then once with saturated aqueous sodium bicarbonate solution. The organic solution was concentrated in vacuo and the residue chromatographed through silica gel 60 (200 g, 230-400 mesh) using an increasing amount of ethyl acetate in heptane (5-50%). The fractions which contained the desired product were combined and washed with saturated aqueous sodium carbonate solution then concentrated in vacuo to provide 1.8 g (18%) of product as a white solid. $^1$H NMR (300 MHz, Gemini 300, CDCl$_3$)δ 4.00 (s, 6H), 3.38 (s, 6H), 2.85 (t, J=6.5 Hz, 6H), 2.59 (t, J=6.5 Hz, 6H), 1.45 (s, 27H), 1.4-1.5 (q, 2H), 0.86 (t, 3H); $^{13}$C NMR (75 MHz, Gemini 300, CDCl$_{13}$, ref. 77.0 ppm)δ 201.3, 172.1, 166.2, 82.0, 63.9, 50.4, 40.7, 37.2, 27.9, 27.7, 22.8, 7.2.

EXAMPLE 4 AND COMPARATIVE EXAMPLES 1, 2, AND 3

Formulations were prepared from compound 3 (prepared as in Example 3) or Cymel 303 and either polyester resin A or B as follows:

| Example | 4 | C-1 | C-2 | C-3 |
|---|---|---|---|---|
| Cymel 303 | — | 8.75 g | 8.75 g | — |
| Compound 3 | 3.08 g | — | — | — |
| Resin A | 9.23 g | — | — | — |
| Resin B | — | 35 g | 35 g | 46.7 g |
| TiO$_2$ R900 | 8.21 g | 29.2 g | 29.2 g | 31.1 g |
| Solvent A | 5.7 mL | — | — | — |
| Solvent B | — | 20 mL | 20 mL | 20 mL |
| Flow Control | 0.05 g | 0.17 g | 0.17 g | 0.10 g |

-continued

| Example | 4 | C-1 | C-2 | C-3 |
|---|---|---|---|---|
| p-TSA | — | 0.13 g | 0.22 g | — |

Solvent A = 50:50 EEP/MAK
Solvent B = 50:30:20 MEK/EEP/MAK
Flow Control = FC-430 as 20% solution in iPrOH
p-TSA = p-Toluenesulfonic acid as 40% solution in iPrOH Coatings of various thicknesses were prepared on phosphated steel panels using a wet film applicator and cured at 150°-180° C. The properties of the resulting formulations are given in Table 1. The improved MEK rub resistance data for Examples 4, C-1, and C-2 relative to C-3 indicate that both compound 4 and Cymel 303 is crosslinking with polyester resins A and B respectively.

TABLE 1

| Ex. # | Cure[a] Conditions | Thickness (mils) | MEK Double Rubs | Pencil Hardness | Impact[b] (F/R) |
|---|---|---|---|---|---|
| 4 | 150/30 | — | 500+ | H | 160/160 |
| 4 | 160/30 | — | 500+ | H | 160/160 |
| 4 | 180/30 | — | 500+ | H | 160/160 |
| C-1 | 150/30 | — | 150 | F | 60/<20 |
| C-1 | 160/30 | — | 100 | F | 40/<20 |
| C-1 | 170/30 | — | 400 | 4H | 160/160 |
| C-1 | 180/30 | — | 400+ | 2H/3H | 160/160 |
| C-2 | 150/30 | — | 200 | H | 60/40 |
| C-2 | 160/30 | 1.82 | 250 | H | 160/160 |
| C-2 | 170/30 | — | 500+ | 3H | 160/160 |
| C-2 | 180/30 | 1.78 | 500+ | 4H | 160/160 |
| C-3 | 150/30 | — | <4 | — | — |
| C-3 | 160/30 | — | <4 | — | — |
| C-3 | 170/30 | 1.35 | <4 | — | — |
| C-3 | 180/30 | 1.45 | <4 | — | — |

[a]Temperature (°C.) and time (min) respectively.
[b]Impact strength in inch-pounds.

We claim:
1. A compound of formula (2)

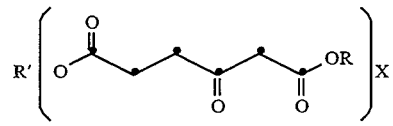

wherein
R is C$_1$-C$_6$ alkyl or phenyl;
R' is the residue of a polyol selected from the group consisting of trimethylolpropane, trimethylolethane, pentaerythritol, glycerin, glucose, sucrose, and a low molecular weight polyol having a Mn of about 250 to 1000; and
X is an integer of from 2 to 12.

2. The compound of claim 1, wherein R is C$_1$-C$_6$ alkyl.

3. The compound of claim 1, wherein R is t-butyl or t-amyl.

4. The compound of claim 1, wherein R' is trimethylolpropane or trimethylolethane.

5. The compound of claim 1, wherein R' is the residue of trimethylolpropane, R is t-butyl, and x is 3.

* * * * *